United States Patent
Qin et al.

(10) Patent No.: US 7,595,410 B2
(45) Date of Patent: Sep. 29, 2009

(54) DIRECT EPOXIDATION PROCESS USING IMPROVED CATALYST COMPOSITION

(75) Inventors: Kun Qin, Chadds Ford, PA (US); Roger A. Grey, West Chester, PA (US); Peter J. Whitman, Glen Mills, PA (US)

(73) Assignee: Lyondell Chemical Technology, L.P., Wilmington, DE (US)

( * ) Notice: Subject to any disclaimer, the term of this patent is extended or adjusted under 35 U.S.C. 154(b) by 693 days.

(21) Appl. No.: 11/489,086

(22) Filed: Jul. 18, 2006

(65) Prior Publication Data

US 2008/0021230 A1    Jan. 24, 2008

(51) Int. Cl.
*C07D 301/06* (2006.01)
*C07D 301/12* (2006.01)

(52) U.S. Cl. .................... 549/532; 549/531

(58) Field of Classification Search ............ 549/531, 549/532

See application file for complete search history.

(56) References Cited

U.S. PATENT DOCUMENTS

| 3,351,635 | A | 11/1967 | Kollar ................ 260/348.5 |
| 4,367,342 | A | 1/1983 | Wulff et al. ............... 549/529 |
| 4,410,501 | A | 10/1983 | Taramasso et al. ......... 423/326 |
| 4,666,692 | A | 5/1987 | Taramasso et al. ......... 423/326 |
| 4,833,260 | A | 5/1989 | Neri et al. ................. 549/531 |
| 4,859,785 | A | 8/1989 | Bellussi et al. ........... 549/531 |
| 4,937,216 | A | 6/1990 | Clerici et al. .............. 502/62 |
| 5,623,090 | A | 4/1997 | Haruta et al. ............. 568/360 |
| 5,859,265 | A | 1/1999 | Müller et al. ............. 549/531 |
| 6,005,123 | A | 12/1999 | Dessau et al. ............. 549/531 |
| 6,008,388 | A | 12/1999 | Dessau et al. ............. 549/531 |
| 6,399,794 | B1 | 6/2002 | Hancu ....................... 549/533 |

FOREIGN PATENT DOCUMENTS

| BE | 1001038 A7 | 6/1989 |
| JP | 4-352771 | 12/1992 |
| WO | WO 98/00413 | 1/1998 |

*Primary Examiner*—Bernard Dentz
(74) *Attorney, Agent, or Firm*—Kevin M. Carroll

(57) ABSTRACT

A process for producing an epoxide comprising reacting an olefin, hydrogen and oxygen in the presence of a catalyst comprising a titanium or vanadium zeolite, palladium, and lead. The process results in significantly reduced alkane by-product formed by the hydrogenation of olefin.

19 Claims, No Drawings

DIRECT EPOXIDATION PROCESS USING IMPROVED CATALYST COMPOSITION

FIELD OF THE INVENTION

This invention relates to an epoxidation process comprising reacting an olefin, hydrogen and oxygen in the presence of a catalyst. The catalyst comprises a titanium or vanadium zeolite, palladium, and lead. Surprisingly, the process results in lower selectivity to undesired alkane byproduct formed by the hydrogenation of olefin compared to similar catalyst systems that do not contain lead.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethylbenzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Another commercially practiced technology is the direct epoxidation of ethylene to ethylene oxide by reaction with oxygen over a silver catalyst. Unfortunately, the silver catalyst has not proved useful in commercial epoxidation of higher olefins.

Besides oxygen and alkyl hydroperoxides, another oxidizing agent useful for the preparation of epoxides is hydrogen peroxide. U.S. Pat. Nos. 4,833,260, 4,859,785, and 4,937,216, for example, disclose the epoxidation of olefins with hydrogen peroxide in the presence of a titanium silicate catalyst.

Much current research is conducted in the direct epoxidation of olefins with oxygen and hydrogen. In this process, it is believed that oxygen and hydrogen react in situ to form an oxidizing agent. Many different catalysts have been proposed for use in the direct epoxidation of higher olefins. Typically, the catalyst comprises a noble metal that is supported on a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form a hydrogen peroxide in situ oxidizing agent. U.S. Pat. No. 5,859,265 discloses a catalyst in which a platinum metal, selected from Ru, Rh, Pd, Os, Ir and Pt, is supported on a titanium or vanadium silicalite. Other direct epoxidation catalyst examples include gold supported on titanosilicates, see for example PCT Intl. Appl. WO 98/00413.

One disadvantage of the described direct epoxidation catalysts is that they are prone to produce non-selective by-products such as glycols or glycol ethers formed by the ring-opening of the epoxide product or alkane by-product formed by the hydrogenation of olefin. U.S. Pat. No. 6,008,388 describes a direct olefin epoxidation process in which the selectivity for the reaction of olefin, oxygen, and hydrogen in the presence of a noble metal-modified titanium zeolite is enhanced by the addition of a nitrogen compound such as ammonium hydroxide to the reaction mixture. U.S. Pat. No. 6,399,794 teaches the use of ammonium bicarbonate modifiers to decrease the production of ring-opened by-products. U.S. Pat. No. 6,005,123 teaches the use of phosphorus, sulfur, selenium or arsenic modifiers such as triphenylphosphine or benzothiophene to decrease the production of propane.

As with any chemical process, it is desirable to attain still further improvements in the epoxidation methods and catalysts. We have discovered an effective, convenient process to form an epoxidation catalyst and its use in the epoxidation of olefins.

SUMMARY OF THE INVENTION

The invention is an olefin epoxidation process that comprises reacting olefin, oxygen, and hydrogen in the presence of a catalyst comprising a titanium or vanadium zeolite, palladium, and lead. This process surprisingly gives significantly reduced alkane by-product formed by the hydrogenation of olefin.

DETAILED DESCRIPTION OF THE INVENTION

The process of the invention employs a catalyst that comprises a titanium or vanadium zeolite, palladium, and lead. Titanium or vanadium zeolites comprise the class of zeolitic substances wherein titanium or vanadium atoms are substituted for a portion of the silicon atoms in the lattice framework of a molecular sieve. Such substances, and their production, are well known in the art. See for example, U.S. Pat. Nos. 4,410,501 and 4,666,692.

Suitable titanium or vanadium zeolites are those crystalline materials having a porous molecular sieve structure with titanium or vanadium atoms substituted in the framework. The choice of titanium or vanadium zeolite employed will depend upon a number of factors, including the size and shape of the olefin to be epoxidized. For example, it is preferred to use a relatively small pore titanium or vanadium zeolite such as a titanium silicalite if the olefin is a lower aliphatic olefin such as ethylene, propylene, or 1-butene. Where the olefin is propylene, the use of a TS-1 titanium silicalite is especially advantageous. For a bulky olefin such as cyclohexene, a larger pore titanium or vanadium zeolite such as a zeolite having a structure isomorphous with zeolite beta may be preferred.

Particularly preferred titanium or vanadium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2$ $(1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

The catalyst employed in the process of the invention optionally comprises a carrier. The carrier is preferably a porous material. Carriers are well-known in the art. For instance, the carrier can be inorganic oxides, clays, carbon, and organic polymer resins. Preferred inorganic oxides include oxides of Group 2, 3, 4, 5, 6, 13, or 14 elements.

Particularly preferred inorganic oxide carriers include silica, alumina, silica-aluminas, titania, zirconia, niobium oxides, tantalum oxides, molybdenum oxides, tungsten oxides, amorphous titania-silica, amorphous zirconia-silica, amorphous niobia-silica, and the like. The carrier may be a zeolite, but is not a titanium or vanadium zeolite. Preferred organic polymer resins include polystyrene, styrene-divinylbenzene copolymers, crosslinked polyethyleneimines, and polybenzimidizole. Suitable carriers also include organic polymer resins grafted onto inorganic oxide carriers, such as polyethylenimine-silica. Preferred carriers also include carbon. Particularly preferred carriers include carbon, silica, silica-aluminas, titania, zirconia, and niobia.

Preferably, the carrier has a surface area in the range of about 1 to about 700 $m^2/g$, most preferably from about 10 to about 500 $m^2/g$. Preferably, the pore volume of the carrier is in the range of about 0.1 to about 4.0 mL/g, more preferably from about 0.5 to about 3.5 mL/g, and most preferably from about 0.8 to about 3.0 mL/g. Preferably, the average particle size of the carrier is in the range of about 0.1 to about 500 µm, more preferably from about 1 to about 200 µm, and most preferably from about 10 to about 100 µm. The average pore diameter is typically in the range of about 10 to about 1000 Å, preferably about 20 to about 500 Å, and most preferably about 50 to about 350 Å.

The catalyst employed in the process of the invention also comprises palladium and lead. The palladium and lead may be added to the catalyst in a variety of ways: (1) the palladium and lead may both be supported on the titanium or vanadium zeolite; (2) palladium and lead may both be supported on an a carrier, and then mixed with titanium or vanadium zeolite to form the catalyst; (3) palladium may be incorporated into the titanium or vanadium zeolite, lead supported on the carrier, and then mixed to form the catalyst; (4) lead may be incorporated into the titanium or vanadium zeolite, palladium supported on the carrier, and then mixed to form the catalyst; or (5) palladium may be incorporated into the titanium or vanadium zeolite, and then mixed with an insoluble lead salt to form the catalyst.

The typical amount of palladium present in the catalyst will be in the range of from about 0.01 to 20 weight percent, preferably 0.01 to 5 weight percent. The manner in which the palladium is incorporated into the catalyst is not considered to be particularly critical. For example, the palladium may be supported on the titanium or vanadium zeolite or the carrier by impregnation or titanium or vanadium zeolite or the carrier by ion-exchange with, for example, palladium tetraammine chloride.

There are no particular restrictions regarding the choice of palladium compound used as the source of palladium. For example, suitable compounds include the nitrates, sulfates, halides (e.g., chlorides, bromides), carboxylates (e.g. acetate), and amine complexes of palladium. Similarly, the oxidation state of the palladium is not considered critical. The palladium may be in an oxidation state anywhere from 0 to +4 or any combination of such oxidation states. To achieve the desired oxidation state or combination of oxidation states, the palladium compound may be fully or partially pre-reduced after addition to the catalyst. Satisfactory catalytic performance can, however, be attained without any pre-reduction. To achieve the active state of palladium, the catalyst may undergo pretreatment such as thermal treatment in nitrogen, vacuum, hydrogen, or air.

The catalyst used in the process of the invention also contains lead. The typical amount of lead present in the catalyst will be in the range of from about 0.001 to 10 weight percent, preferably 0.001 to 2 weight percent. Preferably, the weight ratio of palladium to lead in the catalyst is in the range of 1 to 100. While the choice of lead compound used as the lead source in the catalyst is not critical, suitable compounds include lead carboxylates (e.g., acetate), halides (e.g., chlorides, bromides, iodides), nitrates, cyanides, and sulfides. The lead may be added to the titanium or vanadium zeolite before, during, or after palladium addition, it is preferred to add the lead promoter at the same time that palladium is introduced. Any suitable method can be used for the incorporation of lead into the catalyst. As with palladium addition, the lead may be supported on the titanium or vanadium zeolite or the carrier by impregnation. Incipient wetness techniques may also be used to incorporate the lead.

The catalyst may additionally comprise other noble metals, including gold, platinum, silver, and rhodium. Gold is especially preferred. The typical amount of additional noble metal in the catalyst will be in the range of from about 0.01 to 10 weight percent, preferably 0.01 to 2 weight percent. While the choice of noble metal compound used as the noble metal source in the catalyst is not critical, suitable compounds include noble metal halides (e.g., chlorides, bromides, iodides), oxides, cyanides, and sulfides, as well as more complex species such as tetrachloroauric acid optionally treated with base. The noble metal may be added to the titanium or vanadium zeolite or to the carrier before, during, or after palladium addition. Any suitable method can be used for the incorporation of gold into the catalyst. As with palladium addition, the gold may be supported on the zeolite by impregnation, incipient wetness techniques, or by a deposition-precipitation method (as described in U.S. Pat. No. 5,623,090 for gold compounds).

After palladium, optional noble metal, and lead incorporation, the catalyst is isolated. Suitable catalyst isolation methods include filtration and washing, rotary evaporation and the like. The catalyst is typically dried at a temperature greater than about 50° C. prior to use in epoxidation. The drying temperature is preferably from about 50° C. to about 200° C. The catalyst may additionally comprise a binder or the like and may be molded, spray dried, shaped or extruded into any desired form prior to use in epoxidation.

After catalyst formation, the catalyst may be optionally thermally treated in a gas such as nitrogen, helium, vacuum, hydrogen, oxygen, air, or the like. The thermal treatment temperature is typically from about 20 to about 800° C. It is preferred to thermally treat the catalyst in the presence of an oxygen-containing gas at a temperature from about 200 to 650° C., and optionally reduce the support catalyst in the presence of a hydrogen-containing gas at a temperature from about 20 to 600° C.

The epoxidation process of the invention comprises contacting an olefin, oxygen, and hydrogen in the presence of the catalyst. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$-$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

Oxygen and hydrogen are also required for the epoxidation process. Although any sources of oxygen and hydrogen are suitable, molecular oxygen and molecular hydrogen are preferred.

Epoxidation according to the invention is carried out at a temperature effective to achieve the desired olefin epoxidation, preferably at temperatures in the range of 0-250° C., more preferably, 20-100° C. The molar ratio of hydrogen to oxygen can usually be varied in the range of $H_2:O_2$=1:10 to 5:1 and is especially favorable at 1:5 to 2:1. The molar ratio of oxygen to olefin is usually 2:1 to 1:20, and preferably 1:1 to 1:10. A carrier gas may also be used in the epoxidation process. As the carrier gas, any desired inert gas can be used. The molar ratio of olefin to carrier gas is then usually in the range of 100:1 to 1:10 and especially 20:1 to 1:10.

As the inert gas carrier, noble gases such as helium, neon, and argon are suitable in addition to nitrogen and carbon dioxide. Saturated hydrocarbons with 1-8, especially 1-6, and preferably with 1-4 carbon atoms, e.g., methane, ethane, propane, and n-butane, are also suitable. Nitrogen and saturated $C_1$-$C_4$ hydrocarbons are the preferred inert carrier gases. Mixtures of the listed inert carrier gases can also be used.

Specifically in the epoxidation of propylene, propane or methane can be supplied in such a way that, in the presence of an appropriate excess of carrier gas, the explosive limits of mixtures of propylene, propane (methane), hydrogen, and oxygen are safely avoided and thus no explosive mixture can form in the reactor or in the feed and discharge lines.

The amount of catalyst used may be determined on the basis of the molar ratio of the titanium contained in the titanium zeolite to the olefin that is supplied per unit time. Typically, sufficient catalyst is present to provide a titanium/olefin per hour molar feed ratio of from 0.0001 to 0.1.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

If epoxidation is carried out in the liquid (or supercritical or subcritical) phase, it is advantageous to work at a pressure of 1-100 bars and in the presence of one or more solvents. Suitable solvents include any chemical that is a liquid under reaction conditions, including, but not limited to, oxygenated hydrocarbons such as alcohols, ethers, esters, and ketones, aromatic and aliphatic hydrocarbons such as toluene and hexane, liquid $CO_2$ (in the supercritical or subcritical state), and water. Preferable solvents include water, liquid $CO_2$, and oxygenated hydrocarbons such as alcohols, ethers, esters, ketones, and the like, or mixtures thereof. Preferred oxygenated solvents include lower aliphatic $C_1$-$C_4$ alcohols such as methanol, ethanol, isopropanol, and tert-butanol, or mixtures thereof, and water. Fluorinated alcohols can be used. It is particularly preferable to use mixtures of the cited alcohols with water.

If epoxidation is carried out in the liquid (or supercritical or subcritical) phase, it is advantageous to use a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may range from 3 to 10, preferably from 4 to 9 and more preferably from 5 to 7. Suitable salts of oxyacids contain an anion and cation. The anion portion of the salt may include anions such as phosphate, monohydrogenphosphate, dihydrogenphosphate, sulfate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Examples include $NH_4$, $NBu_4$, $NMe_4$, Li, Na, K, Cs, Mg, and Ca cations. More preferred buffers include alkali metal phosphate and ammonium phosphate buffers. Buffers may preferably contain a combination of more than one suitable salt. Typically, the concentration of buffer in the solvent is from about 0.0001 M to about 1 M, preferably from about 0.001 M to about 0.3 M. The buffer useful in this invention may also include the addition of ammonia gas to the reaction system.

The following examples merely illustrate the invention. Those skilled in the art will recognize many variations that are within the spirit of the invention and scope of the claims.

COMPARATIVE EXAMPLE 1

Preparation of Pd/TS-1 Catalyst

Spray dried TS1 (15.778 pounds; 20 wt. % silica binder, 2.1 wt. % Ti, calcined at 550° C.) is added to deionized water (17.89 L) in a 50 liter mixing tank and stirred by an agitator at 500 rpm. The pH of the slurry is adjusted up to 7.0 using 3% aqueous ammonium hydroxide, then tetraammine palladium nitrate aqueous solution (0.166 pounds Pd, diluted to 1 liter) is added over a one-minute period through a subsurface injection, with agitation. The pH of the slurry is maintained at 7.0 during the palladium addition by adding the 3% ammonium hydroxide solution. After palladium addition, the pH is adjusted up to 7.5 with ammonium hydroxide and the slurry is agitated at 30° C. for 60 minutes while maintaining the pH at 7.4. The slurry is filtered and washed (three times with 17 L of deionized water). The solids are then dried in vacuum at 50° C. until a constant weight is obtained, calcined at 300° C. in air for 1 hour, and then treated with 4% $H_2$ in nitrogen for 1 hour to form Comparative Catalyst 1. Comparative Catalyst 1 contains 0.1 wt. % palladium, 2.1 wt. % titanium and 44 wt. % silicon.

EXAMPLE 2

Preparation OF Pd—Pb/TS-1 Catalyst

Catalyst 1 (8.4 g) and deionized water (25 mL) are placed in a 3-neck 100 mL flask. A lead acetate solution (0.08 g of $Pb(OAc)_2$ in 10 mL of deionized water) is then added to the slurry with stirring, and the reaction mixture was heated at 75-82° C. (using a hot oil bath) and stirred for 45 minutes. The solids are filtered, rinsed four times with deionized water (20 mL each), and dried in a vacuum oven at 65° C. for 2 hours to form Catalyst 2. Catalyst 2 contains 0.08 wt. % palladium, 0.35 wt. % lead, and 2.0 wt. % titanium.

EXAMPLE 3

Insoluble Lead Salts

Catalyst 3A is $PbTiO_3$, a product of Alfa Aesar.
Catalyst 3B is $PbSO_4$, a product of Sigma-Aldrich.
Catalyst 3C is $PbZrO_3$, a product of Sigma-Aldrich.
Catalyst 3D is $PbNiO_3$, a product of Sigma-Aldrich.

EXAMPLE 4

Pd—Pb Supported Catalysts

Catalyst 4A is Pd—Pb/$CaCO_3$, a product of Sigma-Aldrich.
Catalyst 4B is Pd—Pb/$BaSO_4$, a product of Alfa Aesar.

EXAMPLE 5

Preparation of Pd—Au—Pb/$TiO_2$ Catalyst

Pd—Au/$TiO_2$ (4.67 g, made according to the procedure of Example 8A) and deionized water (30 mL) are placed in a 3-neck 100 mL flask. A lead acetate solution (0.030 g of Pb(OAc)$_2$ in 15 mL of deionized water) is then added to the slurry with stirring, and the reaction mixture was heated at 75-85° C. (using a hot oil bath) and stirred for 45 minutes. The solids are filtered, rinsed four times with deionized water (20 mL each), and dried in a vacuum oven at 65° C. for 2.4 hours to form Catalyst 5. Catalyst 5 contains 0.97 wt. % palladium, 0.50 wt. % gold, 0.38 wt. % lead, and 58 wt. % titanium.

EXAMPLE 6

Epoxidation Reaction Using Catalysts from Examples 1-5

To evaluate the performance of the Comparative Catalyst 1 and Catalysts 2, 3A, 3B, 3C, 3D, 4A, 4B, and 5, the epoxidation of propylene using oxygen and hydrogen is carried out. The following procedure is employed:

A reactor system, consisting of a 600-mL pressure reactor and a 1.5 L saturator, is charged with a mixture of methanol (90 g) and 0.1 M ammonium dihydrogenphosphate (30 g) neutralized to pH 6 with dilute ammonium hydroxide. The catalyst or admixtures of catalysts (4.0 g total) are then added to the reactor, and the slurry is heated to 60° C. at 300 psi (2068 kPa). Run 6A uses Catalyst 1 (4 g). Run 6B uses Catalyst 2 (4 g). Run 6C uses a mixture of Catalyst 3A (0.1 g) and Catalyst 1 (3.9 g). Run 6D uses a mixture of Catalyst 3B (0.1 g) and Catalyst 1 (3.9 g). Run 6E uses a mixture of Catalyst 3C (0.1 g) and Catalyst 1 (3.9 g). Run 6F uses a mixture of Catalyst 3D (0.1 g) and Catalyst 1 (3.9 g). Run 6G uses a mixture of Catalyst 4A (0.05 g) and TS-1 (3.95 g). Run 6H uses a mixture of Catalyst 4B (0.2 g) and TS-1 (3.8 g). Run 61 uses a mixture of Catalyst 5 (0.1 g) and TS-1 (3.9 g).

A gaseous feed consisting of 46 cc/min hydrogen, 277 cc/min propylene, and 4318 cc/min of 5% oxygen in nitrogen is introduced into the pressure reactor via a fine frit. The exit gas is analyzed by on-line GC, while PO and ring-opened products in the liquid phase are analyzed at the termination of the reaction. The reaction is carried out for 18 hours, but can be run longer. The results of the GC analyses are used to calculate the productivity and selectivities shown in the Table 1.

COMPARATIVE EXAMPLE 7

Preparation of Pd—Au/$TiO_2$ catalysts

Comparative Catalyst 7A: Aqueous sodium tetrachloro aurate (0.265 g, 20.74 wt. % gold) and solid disodium tetrachloro palladate (0.275 g) are added to deionized water (25 g) with stirring. After the palladium and gold compounds dissolve, anatase $TiO_2$ (10 g, 1 micron average size, 30 m$^2$/g) and sodium bicarbonate (0.25 g) are added to the palladium/gold solution. The slurry is then reacted for 24 h at 23° C., filtered, and the solids are washed with deionized water two times, followed by calcination in air at 220° C. The calcined solids are then washed with deionized water until the final filtrate contains 1 ppm chloride, then dried and calcined in air in a muffle furnace by heating at 10° C./min to 110° C. for 2 h and then heating at 2° C./min to 300° C. for 4 h. The calcined solids are then transferred to a quartz tube and treated with a 4 vol. % hydrogen/nitrogen stream (100 cc/hr) at 100° C. for 3h. Comparative Catalyst 7A contains 0.9 wt. % palladium, 0.55 wt. % gold and 59 wt. % titanium.

Comparative Catalyst 7B: Aqueous sodium tetrachloro aurate (0.265 g, 20.74 wt. % gold) and solid disodium tetrachloro palladate (0.275 g) are added to deionized water (25 g) with stirring. After the palladium and gold compounds dissolve, spray dried anatase $TiO_2$ (10 g, 35 micron average size, 40 m$^2$/g, calcined at 700° C.) and sodium bicarbonate (0.26 g) are added to the palladium/gold solution. The slurry is then reacted for 4 h at 40° C., filtered, and the solids are washed with deionized water (30 g), followed by calcination in air in a muffle furnace by heating at 10° C./min to 110° C. for 6 h and then at 2° C./min to 300° C. for 4 h. The calcined solids are then washed with deionized water (30 g, 6 times), then dried in a vacuum oven at 50° C., and transferred to a quartz tube and treated with a 4 vol. % hydrogen/nitrogen stream (100 cc/hr) at 100° C. for 1 h, and then purged with nitrogen for 1 h. Comparative Catalyst 7B contains 0.95 wt. % palladium, 0.6 wt. % gold and 58 wt. % titanium.

EXAMPLE 8

Preparation of Pd—Au—Pb/$TiO_2$ catalyst

Catalyst 8A: Aqueous sodium tetrachloro aurate (0.265 g, 20.74 wt. % gold) and solid disodium tetrachloro palladate (0.275 g) are added to deionized water (25 g) with stirring. After the palladium and gold compounds dissolve, anatase $TiO_2$ (10 g, 1 micron average size, 87 m$^2$/g) and sodium bicarbonate (0.65 g) are added to the palladium/gold solution to give a pH of 6.3. The pH is adjusted to 7 by the addition of two portions of solid sodium bicarbonate (0.25 g each). The slurry is then reacted for 4 h at 40° C., filtered, and the solids are washed with deionized water (30 g), followed by calcination in air in a muffle furnace by heating at 10° C./min to 110° C. for 6 h and then at 2° C./min to 300° C. for 4 h. The calcined solids are then washed with deionized water (30 g, six times), then dried in a vacuum oven at 50° C., and transferred to a quartz tube and treated with a 4 vol. % hydrogen/nitrogen stream (100 cc/hr) at 100° C. for 1 h, and then purged with nitrogen for 1 h.

The Pd—Au/TiO$_2$ solids (4.67 g) are then slurried in deionized water (30 g), and a solution of lead acetate (0.03 gram) was dissolved in 15 grams of deionized water is added to the slurry. The resulting slurry is stirred at 75 to 85° C. for 45 min, filtered, washed with deionized water (20 g, four times), and dried in a vacuum oven at 65° C. for 2.4 h. Catalyst 8A contains 0.95 wt. % palladium, 0.5 wt. % gold, and 0.4 wt % lead.

Catalyst 8B: Aqueous sodium tetrachloro aurate (0.795 g, 20.74 wt. % gold) and solid disodium tetrachloro palladate (0.825 g) are added to deionized water (120 g) with stirring. After the palladium and gold compounds dissolve, spray dried anatase TiO$_2$ (30 g, 35 micron average size, 43 m$^2$/g, calcined at 700° C.) is added to the palladium/gold solution, followed by the addition of lead acetate (0.22 g). The pH is adjusted to 7.02 by the addition of solid sodium bicarbonate (4.75 g required). The slurry is then reacted for 4 h at 40° C., filtered, and the solids are washed with deionized water (100 g, two times), followed by calcination in air in a muffle furnace by heating at 10° C./min to 110° C. for 6 h and then at 2° C./min to 300° C. for 4 h. The calcined solids are then washed with deionized water (100 g, six times), then dried in a vacuum oven at 50° C. overnight, and transferred to a quartz tube and treated with a 4 vol. % hydrogen/nitrogen stream (100 cc/hr) at 100° C. for 1 h. Catalyst 8B contains 0.95 wt. % palladium, 0.45 wt. % gold, and 0.32 wt % lead.

EXAMPLE 9

Epoxidation Reaction Using Catalysts from Examples 7-8

To evaluate the performance of Comparative Catalysts 7A and 7B and Catalysts 8A and 8B, the epoxidation of propylene using oxygen and hydrogen was carried out. The following procedure is employed:

A 300 cc stainless steel reactor is charged with catalyst (0.07 g) and TS1 powder (0.63 g; 2 wt. % Ti), a buffer (13 g, 0.1 M aqueous ammonium phosphate, pH=6), and methanol (100 g). The reactor is then charged to 300 psig (2068 kPa) of a feed consisting of 2% hydrogen, 4% oxygen, 5% propylene, 0.5% methane and the balance nitrogen (volume %). The pressure in the reactor is maintained at 300 psig (2068 kPa) via a back pressure regulator with the feed gases passed continuously through the reactor at 1600 cc/min (measured at 23° C. and one atmosphere pressure). In order to maintain a constant solvent level in the reactor during the run, the oxygen, nitrogen and propylene feeds are passed through a two-liter stainless steel vessel (saturator), containing 1.5 liters of methanol, preceding the reactor. The reactor is stirred at 1500 rpm. The reaction mixture is heated to 60° C. and the gaseous effluent is analyzed by an online GC every hour and the liquid analyzed by offline GC at the end of the 18 hour run. Propylene oxide and equivalents ("POE"), which include propylene oxide ("PO"), propylene glycol ("PG"), and propylene glycol methyl ethers (PMs), are produced during the reaction, in addition to propane formed by the hydrogenation of propylene. The results of the GC analyses are used to calculate the productivity and selectivities shown in the Table 2.

TABLE 1

Epoxidation Results from Example 6

| Run # | Catalyst | Admixture Component | PO/POE Selectivity (%)[1] | Propylene Selectivity (%)[2] | Productivity[3] |
|---|---|---|---|---|---|
| 6A* | 1 | — | 84.6 | 79.1 | 0.535 |
| 6B | 2 | — | 84.3 | 88.5 | 0.376 |
| 6C | 3A | Pd/TS-1 | 93.7 | 82.8 | 0.549 |
| 6D | 3B | Pd/TS-1 | 87.8 | 83.3 | 0.511 |
| 6E | 3C | Pd/TS-1 | 85.3 | 81.6 | 0.464 |
| 6F | 3D | Pd/TS-1 | 85.9 | 82.2 | 0.529 |
| 6G | 4A | TS-1 | 91.2 | 86.8 | 0.416 |
| 6H | 4B | TS-1 | 78.9 | 92.7 | 0.517 |
| 6I | 5 | TS-1 | 89.1 | 89.2 | 0.453 |

[1]PO/POE Selectivity = moles PO/(moles PO + moles propylene glycols) * 100.
[2]Propylene Selectivity = 100 − (moles propane/moles POE + moles propane) * 100.
[3]Productivity = grams POE produced/gram of catalyst per hour.
*Comparative Example

TABLE 2

Epoxidation Results from Example 9

| Catalyst | PO/POE Selectivity (%)[1] | Propylene Selectivity (%)[2] | Productivity[3] |
|---|---|---|---|
| 7A* | 85 | 47 | 0.91 |
| 8A | 82 | 70 | 0.93 |
| 7B* | 88 | 54 | 0.57 |
| 8B | 89 | 74 | 0.62 |

[1]PO/POE Selectivity = moles PO/(moles PO + moles propylene glycols) * 100.
[2]Propylene Selectivity = 100 − (moles propane/moles POE + moles propane) * 100.
[3]Productivity = grams POE produced/gram of catalyst per hour.
*Comparative Example

We claim:

1. A process for producing an epoxide comprising reacting an olefin, hydrogen and oxygen in the presence of a catalyst comprising titanium or vanadium zeolite, palladium, and lead.

2. The process of claim 1 wherein the titanium or vanadium zeolite is titanium silicalite.

3. The process of claim 1 wherein the catalyst is comprised of from 0.01 to 10 weight percent palladium and from 0.001 to 2 weight percent lead.

4. The process of claim 1 wherein the olefin is a $C_2$-$C_6$ olefin.

5. The process of claim 1 wherein the olefin is propylene.

6. The process of claim 1 wherein the reaction is performed in the presence of a solvent selected from the group consisting of alcohols, ethers, esters, ketones, water, liquid $CO_2$, and mixtures thereof.

7. The process of claim 1 wherein the catalyst comprises palladium and lead supported on the titanium or vanadium zeolite.

8. The process of claim 7 wherein the catalyst comprises palladium, lead, and an additional noble metal supported on the titanium or vanadium zeolite.

9. The process of claim 8 wherein the noble metal is gold.

10. The process of claim 1 wherein the palladium and lead are supported on a carrier.

11. The process of claim 10 wherein the carrier is selected from the group consisting of carbons, titanias, zirconias, niobias, silicas, aluminas, silica-aluminas, tantalum oxides, molybdenum oxides, tungsten oxides, titania-silicas, zirconia-silicas, niobia-silicas, and mixtures thereof.

12. A process for producing propylene oxide comprising reacting propylene, hydrogen and oxygen in the presence of a titanium or vanadium zeolite and a supported catalyst comprising palladium, lead, and a carrier.

13. The process of claim 12 wherein the titanium or vanadium zeolite is a titanium silicalite.

14. The process of claim 12 wherein the supported catalyst is comprised of from 0.01 to 10 weight percent palladium and from 0.001 to 2 weight percent lead.

15. The process of claim 12 wherein the carrier is selected from the group consisting of carbons, titanias, zirconias, niobias, silicas, aluminas, silica-aluminas, tantalum oxides, molybdenum oxides, tungsten oxides, titania-silicas, zirconia-silicas, niobia-silicas, and mixtures thereof.

16. The process of claim 12 wherein the supported catalyst comprises palladium, lead, an additional noble metal, and a carrier.

17. The process of claim 16 wherein the noble metal is gold.

18. The process of claim 12 wherein the reaction is performed in the presence of a solvent selected from the group consisting of alcohols, ethers, esters, ketones, water, liquid $CO_2$, and mixtures thereof.

19. The process of claim 18 wherein the reaction is performed in the presence of a buffer.

* * * * *